(12) United States Patent
Jibiki

(10) Patent No.: US 7,037,655 B2
(45) Date of Patent: May 2, 2006

(54) METHOD OF JUDGING FLOCCULATING PROPERTIES OF BOTTOM BREWER'S YEAST

(75) Inventor: Makiko Jibiki, Ibarakinen (JP)

(73) Assignee: Asahi Breweries, Ltd., Tokyo (JP)

( * ) Notice: Subject to any disclaimer, the term of this patent is extended or adjusted under 35 U.S.C. 154(b) by 549 days.

(21) Appl. No.: 10/148,451

(22) PCT Filed: Nov. 30, 2000

(86) PCT No.: PCT/JP00/08473

§ 371 (c)(1),
(2), (4) Date: May 30, 2002

(87) PCT Pub. No.: WO01/40514

PCT Pub. Date: Jun. 7, 2001

(65) Prior Publication Data

US 2004/0214169 A1 Oct. 28, 2004

(30) Foreign Application Priority Data

Nov. 30, 1999 (JP) ................................. 11/338935

(51) Int. Cl.
- C12Q 1/68 (2006.01)
- C12P 19/34 (2006.01)
- C07H 21/02 (2006.01)
- C07H 21/04 (2006.01)

(52) U.S. Cl. .................. 435/6; 435/91.2; 536/23.5; 536/24.31; 536/24.33

(58) Field of Classification Search .................. 435/6, 435/91.1, 91.2; 536/23.1, 24.1
See application file for complete search history.

(56) References Cited

U.S. PATENT DOCUMENTS 5,585,271 A * 12/1996 Watari et al. ............ 435/254.2

FOREIGN PATENT DOCUMENTS

FR WO-99/52942 * 10/1999

OTHER PUBLICATIONS

Pennisi et al. Science, 281 (5384):1787-1789.*
Hacker et al. Gut, 1997, vol. 40, pp. 623-627).*
Yamagishi et al.(Journal of Applied Microbiology (1999), 86, 505-513.*
Bidard et al.(Cur Genet(1994) 25: 196-201).*

* cited by examiner

Primary Examiner—W. Gary Jones
Assistant Examiner—Sally Sakelaris
(74) Attorney, Agent, or Firm—Browdy and Neimark, PLLC

(57) ABSTRACT

The present invention provides a reproducible method to determine flocculating properties of bottom fermenting yeast, at a short time, easily and quickly, without fermentation. It is characterized in using an ORF sequence of a flocculation gene FLO5 of laboratory's yeast (*Saccharomyces cerevisiae*).

4 Claims, 2 Drawing Sheets strain  a  b  c  d  Size Marker (λ BstP I)

Strength of flocculating property by Burns test

+ > + > ± > ± > −

— 7242 bp
— 6369
— 5687
— 4822
— 4324
— 3675
— 2323

Flocculating property by Burns test    +    − about 9.3Kb →

+···flocculent
−···non-flocculent

METHOD OF JUDGING FLOCCULATING PROPERTIES OF BOTTOM BREWER'S YEAST

TECHNICAL FIELD

The present invention relates to a method to determine presence of flocculating properties of bottom fermenting yeast (brewer's lager yeast) or detecting genetical change to the non-flocculent.

BACKGROUND ART

Beer of a lager type is produced in Japan, Germany and the other countries. Most yeast, which is used for beer brewing of this type, have flocculation properties at the latter period of the brewing and sedimentation properties at the bottom of a tank, so that it is called bottom fermenting yeast. The sedimentation properties of the yeast are important for the influence against recovery and then filtration of the yeast, and flavor and quality of beer in beer brewing. Further, when the properties of the bottom fermenting yeast are stabilized, the yeast has the advantage that it can be repeatedly used as recovery yeast in the beer production steps. In such cases, it is important to determine flocculating properties of bottom fermenting yeast in screening and selection of new yeast.

As a common method to determine flocculating properties of yeast, there are many methods such as a Burns method (J. Inst. Brew., 43, 31, 1937), a Helm method (Wallerstein Laboratory Communications 16, 315, 1953) and the like. In these methods, after culturing and fermenting yeast, collected yeast is artificially flocculated under an atmosphere that the yeast is easily flocculated and sedimented in the presence of Ca ions. By these methods, the flocculation and sedimentation property is determined.

When flocculation property of yeast is decreased or disappeared in the actual beer production steps, it needs to determine whether collected yeast can be repeatedly used or not. For the determination that the non-flocculation is caused by an irreversible change of yeast itself, namely by a mutation, or by a reversible change of not yeast but environment, it takes about two weeks to obtain the results because such a method to determine flocculating properties should be conducted after culturing and fermenting yeast under certain conditions to evaluate.

Mutation of yeast is not caused in all cells at the same time. It is important to isolate single colonies, study the flocculating properties and know the population of mutants. However, in the method to determine flocculating properties, after conventional culturing and fermentation, it is difficult to treat many strains at a time.

In recent years, DNA sequences of laboratory's yeast (*Saccharomyces cerevisiae*) were made clear in all chromosomes, the presence of several genes participating in flocculating properties was confirmed (Science 274, 546(1996), Nature 387, 7(1997)). In these genes, FLO1 gene on the chromosome I was studied most, and the gene was isolated and analyzed (Japanese Patent Hyohei-7-509372, Yeast, 9, 1 (1993), Yeast, 10, 211 (1994)). The isolation and analysis of FLO5 gene were also reported that the gene was on a different chromosome from FLO1 gene and has high homologous DNA sequences (Science, 265, 2077 (1994), Curr. Genet., 25, 196 (1994)). The isolation and analysis of FLO8 gene also were reported (Agric. Biol. Chem., 47, 2889 (1983), Mol. Gen. Genet., 251, 707 (1986)).

It was found that bottom fermenting yeast had chromosomes derived from both *Saccharomyces cerevisiae* and *Saccharomyces bayanus*. However, it was not successful in determination of the flocculating properties of the bottom fermenting yeast by noticing a gene derived from the both yeast (Yeast, 14, 923 (1998), System. Appl. Microbial. in Press (1999)).

In a method that FLO1 and FLO8 genes of *Saccharomyces cerevisiae* having flocculating properties were noticed, it was not successful in determination of flocculating properties of beer yeast. Further, it was recently found a part of genes having the flocculating properties of beer yeast. It is reported that, by presence of a part of DNA sequences of the genes, presence of the flocculating properties of the beer yeast type can be determined. It is not reported, however, that decrease and disappearance of the flocculating properties can be determined by genetical change of the yeast (Japanese Patent Laid-open Hei 8-205900).

DISCLOSURE OF THE INVENTION

The present invention aims to easily obtain a method to determine presence of flocculating properties of bottom fermenting yeast at a short time by excellent reproductivity.

By using the primer designed under an ORF sequence of a flocculation gene FLO5 on the chromosome VIII of laboratory's yeast (*Saccharomyces cerevisiae*) (Science, 265, 2077 (1994)), PCR was conducted to search the presence of amplification of the objective fraction and the size. By using a template of genome of flocculating bottom fermenting yeast, PCR is conducted by the above-mentioned primer and resultant amplified products is used as a probe for Southern hybridization. By these steps, it is found that it is able to determine the presence of flocculation properties of bottom fermenting yeast and to detect a genetical change to non-flocculating properties.

Namely, the first invention is a method to determine the presence of flocculating properties of bottom fermenting yeast by using an ORF sequence of a flocculation gene FLO5 of laboratory's yeast (*Saccharomyces cerevisiae*).

The second invention is a method to determine non-flocculating properties and decrease of flocculating properties by genetical change of bottom fermenting yeast having original flocculating properties, by using the ORF sequence.

The third invention is a method for foreknowing non-flocculating properties and decrease of flocculating properties by genetical change of bottom fermenting yeast having original flocculating properties, by using the sequence.

The fourth invention is a method to determine the presence of flocculating properties of bottom fermenting yeast, wherein the primer designed from the sequence is used, and a PCR reaction is conducted to detect the presence of amplified products.

The fifth invention is a method to determine non-flocculating properties and decrease of flocculating properties by genetical change of bottom fermenting yeast, wherein the primer designed from the sequence is used, a PCR reaction is conducted to detect the presence of amplified products.

The sixth invention is a method for foreknowing the presence of non-flocculating properties and decrease of flocculating properties by genetical change of bottom fermenting yeast, wherein the primer designed from the ORF sequence is used, and a PCR reaction is conducted to compare the sizes of DNA of amplified products of a yeast strain showing flocculating properties.

The seventh invention is a method to determine non-flocculating properties and decrease of flocculating properties by genetical change of bottom fermenting yeast, wherein several single colonies are isolated from the yeast, a PCR reaction is conducted by using the primer designed from the sequence, and the population of variants in the yeast is grasped.

The eighth invention is a method for foreknowing non-flocculating properties and decrease of flocculating properties by genetical change of bottom fermenting yeast, wherein several single colonies are isolated from the yeast, a PCR reaction is conducted by using the primer designed from the sequence, and the population of variants in the yeast is grasped.

The ninth invention is a method to determine the presence of flocculating properties of bottom fermenting yeast, wherein all DNA of the bottom fermenting yeast having flocculating properties are used as a template, the primer designed from the sequence is used, and a PCR reaction is conducted to use the amplified products.

The tenth invention is a method to determine the non-flocculating properties by genetical change of bottom fermenting yeast, wherein all DNA of the bottom fermenting yeast having flocculating properties are used as a template, the primer designed from the sequence is used, and a PCR reaction is conducted to use the amplified products.

BEST MODE FOR CARRYING OUT THE INVENTION

Figure 1:
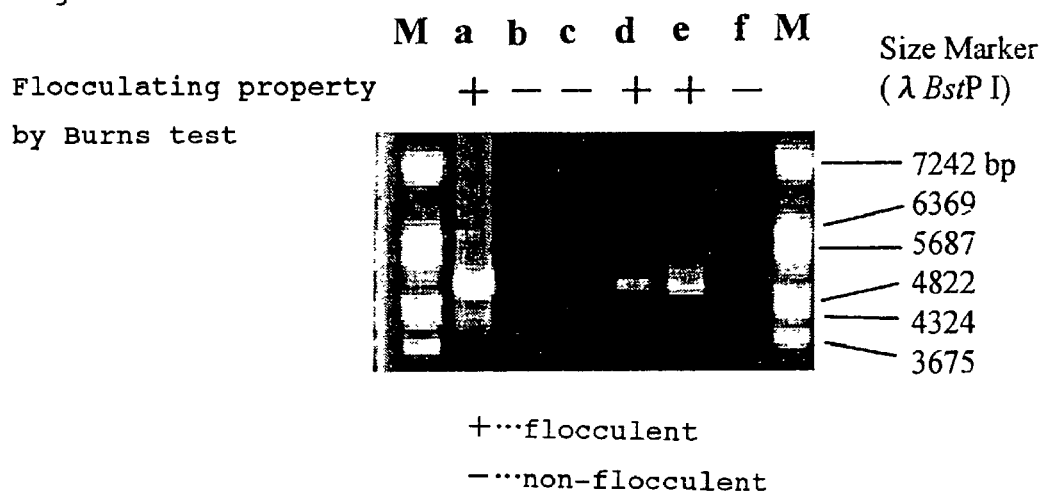
FIG. 1 is an electrophoretogram showing flocculating properties of several kinds of bottom fermenting yeast and PCR amplified products.

The present invention provides a method to determine flocculating properties of yeast in several levels of bottom fermenting yeast and variants' levels that the variants are derived from flocculent lager yeast. The method uses a DNA sequence or the complementary sequence of ORF region (3228 bp) of flocculation gene FLO5 on the chromosome VIII of laboratory's yeast (*Saccharomyces cerevisiae*). Namely, the present invention is a method to determine the flocculating properties by investigation of the presence of genes necessary to development of flocculating properties of yeast.

The present invention is described in detail in the following. Any known methods can be used in the production of an objective yeast DNA (for example, Methods in Yeast Genetics, Cold Spring Harbor Laboratory Press, p130 (1990)). When the DNA is prepared from many samples, automatic DNA extraction device, which remarkably has progressed, is efficient and the operation is easy.

The presence of genes can be confirmed by any methods known hitherto. The main methods are described in the following.

① Nucleic acid was amplified by a PCR method using a primer pair comprising continuous bases of 10 bp or more as a template of a DNA which was extracted from objective yeast. To obtain high stable detection sensitivity, the primer length is preferably about 20 bp. When combined primers are designed, one primer comprises a DNA molecule of 0—about 2000 bp at the C end or a DNA molecule that contains a DNA sequence complementary to the DNA molecule of 0—about 2000 bp, and another primer comprises a DNA molecule of about 2400–3228 bp at the N end or a DNA molecule that contains a DNA sequence complementary to the DNA molecule of about 2400–3228 bp. Examples of the primers show in Table 1. When the sequence of the C end is selected as a sense sequence, any sequence of the N end can be selected as an antisense sequence. In the examples of primers, namely, sequence c or sequence d may be selected to determine yeast for sequence a. Sequence c or sequence d may be similarly selected for sequence b. Sequence a corresponds to sequence No.1, sequence b to sequence No.2, sequence c to sequence No.3 and sequence d to sequence No.4. The above-described DNA molecule can be chemically synthesized by known methods. Such synthesis may be trusted to a professional.

Any polymerase may be used in the PCR reaction, and polymerase having excellent thermostable properties, which can amplify to obtain a stable long chain, is preferably used. A kit containing a mixture except a primer pair and a genome to be determined, for example, TaKaRa Perfect Shot (produced by Takara Shuzo) is effectively used to easily obtain stable results. The reaction conditions are common PCR conditions, for example, thermal denaturation temperatures of 90–95° C., annealing temperatures of 40–65° C., elongation temperatures of 70–75° C., and above 20 cycles, preferably.

The resulting amplified products are separated by electrophoresis using agarose gel and the like in the usual way and detected by ethidium bromide.

② DNAs prepared from yeast having flocculating properties are used as a template, and nucleic acids are amplified by the PCR method using the above-mentioned primer. The resulting amplified products are simply purified by known methods, and labeled with a radioisotope, a fluorochrome or the like. Using the product as a probe, the yeast genome to be determined is separated by electrophoresis and hybridized with a sample blotted on a membrane. Hybridized conditions are detected by fitting to an adopted labeling method.

EXAMPLES

The present invention is more concretely described by examples in the following. However, the present invention is not limited by these examples.

Example 1

Determination of Flocculating Properties of Bottom Fermenting Yeast

① Extraction of Yeast DNA

Bottom fermenting yeast 30 strains were respectively cultured in 10 ml of YPD medium (1% Yeast Extract, 2% Peptone, 2% Dextrose) until the stationary phase, and the yeast was collected by centrifugation. After washing with distilled water, the yeast was collected. The yeast was suspended in 0.2 ml of a solution of 2% Triton X-100, 1% SDS, 100 mM NaCl, 10 mM Tris-HCl (pH 8.0), and 1 mM $Na_2EDTA$. Further, 0.2 ml of phenol-chloroform-isoamylalcohol (25:24:1) and 0.3 g of glass beads, which were washed with aqueous acid, were added to the suspension and the mixture was thoroughly stirred for 3 minutes. After 0.2 ml of TE (10 mM Tris-HCl (pH 7.5), 1 mM EDTA) was added, the mixture was centrifuged for 5 minutes. After the aqueous phase was separated, 1 ml of 100% ethanol was added to the residue and left for 10 minutes or more at −20° C., and the sediment was recovered by centrifugation. The resulting sediment was dissolved in 0.4 ml of the above TE, 3 μl of 10 mg/ml RNAse A solution was added, and the mixture was warmed for 5 minutes at 37° C. After adding 10 μl of 4M ammonium acetate and 1 ml of 100% ethanol, the mixture was left for 10 minutes or more at −20° C., and the sediment was recovered by centrifugation. The resulting sediment was dissolved in 50 μl of distilled water, and a part of the solution was tested.

② Determination of Flocculating Properties by a PCR Method with a Part of FLO5 Sequences of a Gene Having Flocculating Properties Primer pairs were designed with ORF sequences of gene FLO5 having flocculating properties on the chromosome VIII of Saccharomyces cerevisiae. Examples of such primer pairs were shown in Table 1. PCR reaction was conducted under conditions: hot start was 94° C. and 2 minutes; 94° C. and 1 minute, 57.5° C. and 2 minutes, 72° C. and 2 minutes were repeated in 30 cycles; and the finish was 72° C. and 20 minutes. A part thereof was taken out to be used for electrophoresis with 1% agarose gel. On the other hand, the same strains were cultured in YPD medium and fermented in wort, and the flocculating properties were determined by the above Burns method. The method is that flocculating properties of yeast are artificially developed in the presence of Ca ion accelerating the flocculation under the conditions suit to flocculate and sediment the yeast, and the flocculated and sedimented property is determined. Flocculation properties are determined by the amount of sediments. A part of the results amplified by the PCR method using primer pair a and c is shown in FIG. 1. It shows that the presence of about 5,000 bp of amplified DNA is in accord with the results determined by the Burns method. According to the present invention, it becomes possible to determine the difference between flocculating strains (Bruchhefe) and nonflocculating strains (Staubhefe) of bottom fermenting yeast. According to the present invention, it becomes possible to determine the flocculating properties of bottom fermenting yeast at a short time, and it is confirmed that such determination may be a method for screening.

TABLE 1

| primer | | DNA sequences |
|---|---|---|
| a | sense | 5' ATGACAATTGCACACCACTG 3' |
| b | sense | 5' ATTTCCTCCTCAGTAATTTC 3' |
| c | antisense | 5' TTAAATAATTGCCAGCAATA 3' |
| d | antisense | 5' CATGAGATTCGCAGGATGTC 3' |

Example 2

Evaluation of Flocculating Variants of Bottom Fermenting Yeast

Flocculating strains and nonflocculating strains sponteneously lost their flocculating properties derived from three kinds of flocculating lager yeast, these strains were cultured by the method shown in Example 1 until the stationary phase, and the DNA was extracted. Similarly, using the primer pairs in the above Table 1, the PCR reaction was conducted. Amplified products were used for electrophoresis.

Figure 2:
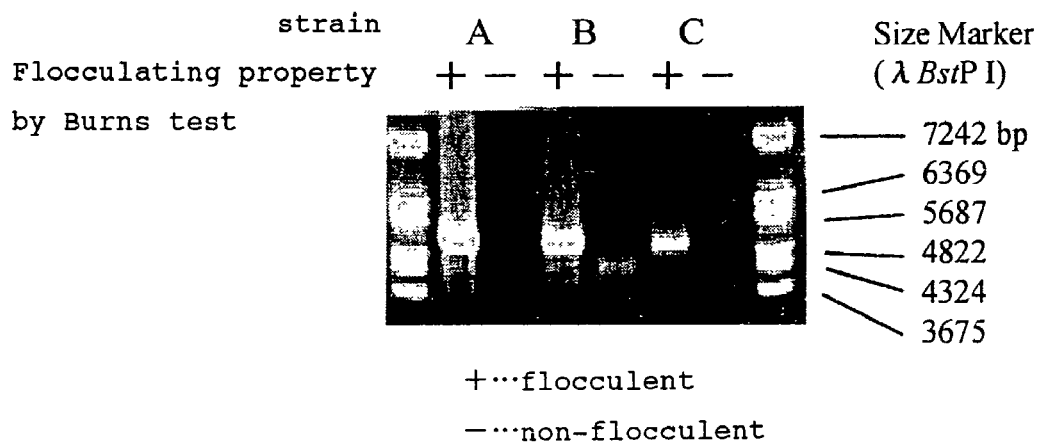
FIG. 2 is an electrophoretogram showing PCR amplified products of flocculating strains and nonflocculating strains, which are derived from bottom fermenting yeast having flocculating properties.

A part of the results were shown in FIG. 2. It is confirmed that flocculating cells and nonflocculating cells can be determined by the presence or absence of amplified DNA of about 5,000 bp and the flocculating variants can be evaluated. Any primer pairs including those of both sides of FLO5 sequences (primers a and c) can be used for determination of the presence of flocculating properties.

Example 3

Population Search of Variants Occupied in Yeast Groups

① Isolation of Single Colonies and Extraction of Yeast DNA

Three yeast groups derived from the same yeast strain having different flocculating properties during beer fermentation were respectively applied on YPD plate mediums (1% Yeast Extract, 2% Peptone, 2% Dextrose, and 2% Agarose), and cultured for 3 days at 25° C. to isolate several tens single colonies respectively. Using the method described in Example 1, each single colony was cultured until the stationary phase. The resulting yeast was collected, and washed to extract the yeast DNA with an automatic DNA extraction device (Toyobo Mag-Extractor II).

② Determination of Flocculating Properties by the PCR Method

Using the above method, PCR reaction was conducted by using the same primer pairs as shown in Table 1, and amplified products were subjected to electrophoresis.

Figure 3:
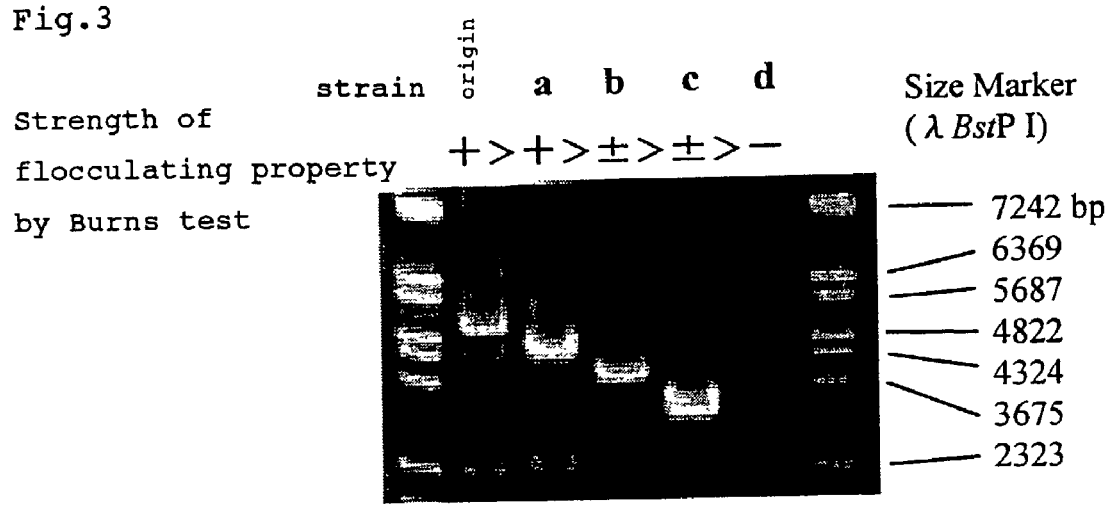
FIG. 3 is an electrophoretogram showing the relation between a size of PCR amplified products of the strains derived from bottom fermenting yeast having flocculating properties, and the flocculating strength.

A part of the results, namely the results using primer pair a and c are shown in FIG. 3. The presence of DNA amplified products of about 5,000 bp and the presence of amplified products having different band sizes were confirmed. Strains of different size of amplified products obtained by the PCR were supplied to fermentation test using wort in a small scale of 50 ml, and the flocculating properties were determined by the above Burns method. As the results, coincidence was found between the presence of amplified DNA fragments of about 5,000 bp and the presence of the flocculating properties. Poor flocculating properties were confirmed in the strains having shortened amplification DNA fragments. According to the method, it is possible to detect not only the strains lost the flocculating properties but the strains possible to decrease or lose the flocculating properties, which have never been reported by this time.

③ Population Search of Variants

From the above results, as shown in Table 2, it was confirmed that three yeast groups had different rates of flocculating strains. The yeast group of excellent flocculating properties showed a high rate of flocculating strains, and the yeast group of poor flocculating properties showed a low rate of flocculating strains. The yeast group of low rate of flocculating strains had many yeast cells in wort during the fermentation, and it was expected that the yeast collection was difficult after the fermentation. By using the present method, it was possible to know the rate of flocculating variants that was influential in practice.

TABLE 2

| yeast groups | A | B | C |
|---|---|---|---|
| flocculating of the latter period | excellent | a little bad | bad |
| rate of flocculating strains | 100% | 68% | 37% |

Example 4

Method for Determination of Flocculating Properties of Bottom Fermenting Yeast by Southern Hybridization After culturing flocculating strains and nonflocculating strains produced by spontaneous mutation derived from flocculating yeast in a YPD medium until the stationary phase, all DNA were extracted by a method described in Methods in Cell Biology (Academic Press Vol. 12, p39–44, 1975). Extracted DNA was digested with a restriction enzyme of EcoRI or BamHI (Takara Shuzo), electrophoresed with 1% agarose gel, and blotted on nylon membrane high bond N+ (produced by Amasham Pharmacia) to conduct Southern analysis.

Using flocculating yeast DNA as a template, the product was amplified by the PCR method using the primer pairs of the above Table 1. The amplified product was separated by electrophoresis in 1% agarose gel. The fragment of about 5,000 bp was cut under ultraviolet irradiation, and DNA was extracted with QIA quick Gel Extraction Kit (QIAGEN Company). Using the extract as a probe, the detection was conducted with an ECL detection system as shown in the protocol.

Figure 4:
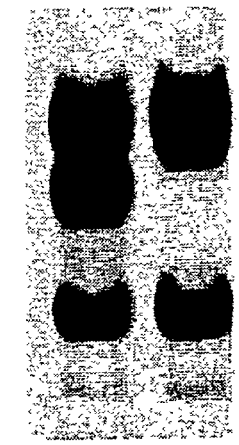
FIG. 4 is a photograph showing a result of Southern analysis of flocculating strains, which are derived from bottom fermenting yeast having flocculating properties, and nonflocculating strains.

The amplified fragment obtained by PCR using the primer pair a and c was used as a probe. The results were shown in FIG. 4. About 9.3 kb, which was found in the flocculating strain, was not found in the nonflocculating strain. Accordingly, it is possible to determine flocculating properties by using the present invention.

INDUSTRIAL USING POSSIBILITY

Using the present invention, it is possible to provide an accurate method to determine the presence of flocculating properties of bottom fermenting yeast and detecting the nonflocculating variants at a short time, easily and quickly, without fermentation of the bottom fermenting yeast. Many samples can be treated at a time, so that the method is useful in research and development of the yeast, and process control and quality control of the industrial production.

The invention claimed is:

1. A method to determine the presence of flocculating properties of bottom fermenting yeast of characterized in that sample yeast strains are cultured, DNA is extracted, and a PCR reaction is conducted with the DNA by using a primer set of continuous bases of 10 bp or more, which is designed from an ORF sequence of a flocculation gene FLO5 of *Saccharyomyces cerevisiae*, to detect the presence of amplified products, wherein the primer set comprises a first primer of SEQ ID NO:1 or 2 and a second primer of SEQ ID NO:3 or 4.

2. The method of claim 1, wherein, in the primer set, the first primer is SEQ ID NO:1 and the second primer is SEQ ID NO:3.

3. A method to determine the presence of flocculating properties of bottom fermenting yeast, characterized in that, using flocculating yeast DNA as a template, using as a probe the products amplified by a PCR reaction, in which it is conducted by using a primer set of continuous bases of 10 bp or more, which is designed from an ORF sequence of a flocculation gene FLO5 of *Saccharyomyces cerevisiae*, hybridization is conducted with the DNA extracted from cultured sample yeast, wherein the primer set comprises a first primer of SEQ ID NO:1 or 2 and a second primer of SEQ ID NO:3 or 4.

4. The method of claim 3, wherein, in the primer set, the first primer is SEQ ID NO:1 and the second primer is SEQ ID NO:3.

* * * * *

```
                      SEQUENCE LISTING

<160> NUMBER OF SEQ ID NOS: 4

<210> SEQ ID NO 1
<211> LENGTH: 20
<212> TYPE: DNA
<213> ORGANISM: Saccharomyces cerevisiae

<400> SEQUENCE: 1
atgacaattg cacaccactg                                           20

<210> SEQ ID NO 2
<211> LENGTH: 20
<212> TYPE: DNA
<213> ORGANISM: Saccharomyces cerevisiae

<400> SEQUENCE: 2 atttcctcctc agtaatttc                                           20

<210> SEQ ID NO 3
<211> LENGTH: 20
<212> TYPE: DNA
<213> ORGANISM: Saccharomyces cerevisiae

<400> SEQUENCE: 3
ttaaataatt gccagcaata                                           20

<210> SEQ ID NO 4
<211> LENGTH: 20
<212> TYPE: DNA
<213> ORGANISM: Saccharomyces cerevisiae

<400> SEQUENCE: 4
catgagattc gcaggatgtc                                           20
```